(12) United States Patent
Svendsen et al.

(10) Patent No.: US 6,960,459 B2
(45) Date of Patent: *Nov. 1, 2005

(54) CUTINASE VARIANTS

(75) Inventors: Allan Svendsen, Hørsholm (DK);
Sanne O. Schroder Glad, Ballerup (DK); Shiro Fukuyama, Chiba (JP);
Tomoko Matsui, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 70 days.

This patent is subject to a terminal disclaimer.

(21) Appl. No.: 09/873,075

(22) Filed: Jun. 1, 2001

(65) Prior Publication Data

US 2002/0123123 A1 Sep. 5, 2002

Related U.S. Application Data

(60) Provisional application No. 60/265,473, filed on Jan. 31, 2001, provisional application No. 60/253,798, filed on Nov. 29, 2000, provisional application No. 60/244,351, filed on Oct. 30, 2000, and provisional application No. 60/211,004, filed on Jun. 12, 2000.

(30) Foreign Application Priority Data

| Jun. 2, 2000 | (DK) | 2000 00861 |
|---|---|---|
| Oct. 23, 2000 | (DK) | 2000 01577 |
| Nov. 24, 2000 | (DK) | 2000 01772 |
| Jan. 19, 2001 | (DK) | 2001 00100 |

(51) Int. Cl.$^7$ ............... C12N 9/18; C07H 21/04
(52) U.S. Cl. ............... 435/197; 536/23.2
(58) Field of Search ............... 435/197, 198; 536/23.2; 424/94.6

(56) References Cited

U.S. PATENT DOCUMENTS 5,827,719 A  10/1998  Sandal et al. ............... 435/198

FOREIGN PATENT DOCUMENTS

| WO | WO 90/09446 | 8/1990 |
| WO | WO 9414963 | 7/1994 |
| WO | WO 9414964 | 7/1994 |
| WO | WO 9727237 | 7/1997 |
| WO | WO 0005389 | 2/2000 |
| WO | WO 00/34450 | 6/2000 |

OTHER PUBLICATIONS

Juffer et al., Journal of Computational Chemistry, Vo. 17, No. 16, 1783–1803, 1996.
Martinez et al., Protein Engineering, vol. 6, No. 2, 157–165, (1993).
Longhi et al., Protein Structure, Function, and Genetics; vol., 26; 442–459.
Biotechniques; vol. 27 1102–1108 (1999).
Longhi et al., Journal of Molecular Biology; vol. 268/4; 779–799 (1997).
Longhi et al., Biochemoci et biophysica acta; vol. 1441; 185–196 (1999).
Borgstrom et al., Lipases; H.L. Elsevier, 471–504, (1984).
Nicolas et al., Biochemistry, vol. 35, 398–410, (1996).
Petersen et al., Journal of Biotechnology, vol. 66; 11–26 (1998).
Creveld et al., Proteins: Structure, Function, and Genetics; vol. 33; 253–264 (1998).
Sagt et al., Environmental Microbiology, vol. 64/1; 316–324 (1998).
Gemeren et al., Environmental Microbiology, vol., 64/8; 2794–2799 (1998).
Flipsen et al., Chemistry and Physics of Lipids, vol. 97; (1999) 181–191.
Jelsch et al., Proteins: Structure, Function, and Genetics 31:320–333 (1998).

*Primary Examiner*—Elizabeth Slobodyansky
(74) *Attorney, Agent, or Firm*—Jason I. Garbell; Elias J. Lambris

(57) ABSTRACT

Variants of fungal cutinases having improved thermostability comprise substitution of one or more specified amino acid residues and/or a specified N-terminal extension. The variants may optionally comprise additional alterations at other positions.

28 Claims, No Drawings

US 6,960,459 B2

CUTINASE VARIANTS

CROSS-REFERENCE TO RELATED APPLICATIONS

This application claims, under 35 U.S.C. 119, priority of Danish application nos. PA 2000 00861, filed Jun. 2, 2000, PA 2000 01577, filed Oct. 23, 2000, PA 2000 01772, filed Nov. 24, 2000, and PA 2001 00100, filed Jan. 19, 2001, and U.S. application Ser. No. 60/211004, filed Jun. 12, 2000, U.S. Ser. No. 60/244351, filed Oct. 30, 2000, U.S. Ser. No. 60/253798, filed Nov. 29, 2000, and U.S. Ser. No. 60/265473, filed Jan. 31, 2001, the contents of which are fully incorporated herein by reference.

FIELD OF THE INVENTION

The present invention relates to a cutinase variant, more particularly to a cutinase variant having improved thermostability. The invention also relates to a DNA sequence encoding the variant, a vector comprising the DNA sequence, a transformed host cell harboring the DNA sequence or the vector, to a method of producing the variant, and to use of the variant.

BACKGROUND OF THE INVENTION

Cutinases are lipolytic enzymes capable of hydrolyzing the substrate cutin. Cutinases are known from various fungi (P. E. Kolattukudy in "Lipases", Ed. B. Borgström and H. L. Brockman, Elsevier 1984, 471–504). The amino acid sequence and the crystal structure of a cutinase of *Fusarium solani* pisi have been described (S. Longhi et al., Journal of Molecular Biology, 268 (4), 779–799 (1997)). The amino acid sequence of a cutinase from *Humicola insolens* has also been published (U.S. Pat. No. 5,827,719).

A number of variants of the cutinase of *Fusarium solani* pisi have been published: WO 94/14963; WO 94/14964; WO 00/05389; Appl. Environm. Microbiol. 64, 2794–2799, 1998; Proteins: Structure, Function and Genetics 26, 442–458, 1996; J. of Computational Chemistry 17, 1783–1803, 1996; Protein Engineering 6, 157–165, 1993; Proteins: Structure, Function, and Genetics 33, 253–264, 1998; J. of Biotechnology 66, 11–26, 1998; Biochemistry 35, 398–410, 1996; Chemistry and Physics of Lipids 97, 181–191, 1999; Proteins: Structure, Function, and Genetics 31, 320–333, 1998; Biochimica et Biophysica Acta 1441, 185–196, 1999; Appl. Environm. Microbiol. 64, 316–324, 1998; BioTechniques 27, 1102–1108, 1999.

Fungal cutinases may be used in the enzymatic hydrolysis of cyclic oligomers of poly(ethylene terephthalate), e.g. in the finishing of yarn or fabric from poly(ethylene terephthalate) fibers (WO 97/27237). It is desirable to improve the thermostability of known fungal cutinases to allow a higher process temperature.

SUMMARY OF THE INVENTION

The inventors have found certain variants of fungal cutinases having improved thermostability. The variants comprise substitution of one or more amino acid residues at positions corresponding to Q1, L2, A4, G8, S11, N15, A16, T29, V38, N44, S48, H49, L66, A88, N91, S116, S119, G120, A130, Q139, T164, T166, L167, I168, I169, L174, I178, R189 and/or the N-terminal extension AAVDSNHT-PAVPELVAR (SEQ ID NO: 2). The variants may optionally comprise additional alterations at other positions.

The invention also provides a DNA sequence encoding the variant, an expression vector comprising the DNA sequence, a transformed host cell harboring the DNA sequence or the expression vector, a method of producing the variant, processes using the variant and a detergent composition comprising the variant.

Further, the invention provides a method of producing cutinase variants by introducing amino acid alterations (substitution, deletion or insertion) at one or more of the indicated positions or in a region comprising such position, and selecting variants with improved thermostability. The alterations may be made, e.g., by localized random mutagenesis or by site-directed mutagenesis.

DETAILED DESCRIPTION OF THE INVENTION

Fungal Cutinase

The parent enzyme is a cutinase classified as EC 3.1.1.74 according to Enzyme Nomenclature. It is a fungal cutinase, such as a filamentous fungal cutinase, e.g. native to a strain of *Humicola* or *Fusarium*, specifically *H. insolens* or *F. solani* pisi, more specifically *H. insolens* strain DSM 1800.

SEQ ID NO: 1 shows the amino acid sequence of the cutinase of *H. insolens* strain DSM 1800 (the mature peptide) and the numbering system used herein for the *H. insolens* cutinase. The amino acid sequence and the DNA sequence encoding it were previously published as SEQ ID NO: 2 and SEQ ID NO: 1 of U.S. Pat. No. 5,827,719, which are herein incorporated by reference.

The amino acid sequence of the cutinase of *F. solani* pisi is shown as the mature peptide in FIG. 1D of WO 94/14964, which is herein incorporated by reference. The numbering system used herein for the *F. solani* pisi cutinase is that used in WO 94/14964; it includes the pro-sequence shown in said FIG. 1D; thus, the mature cutinase is at positions 16–215.

The parent cutinase may have an amino acid sequence which is at least 50% (particularly at least 70% or at least 80%) homologous to the cutinase of *H. insolens* strain DSM 1800. The parent cutinase may particularly be one that can be aligned with the cutinase of *H. insolens* strain DSM 1800.

The present invention also relates to isolated cutinase variants, as described herein, in which the cutinase variant is encoded by a nucleic acid sequence, which hybridizes under high, medium, or low stringency conditions with the nucleic acid sequence encoding the cutinase of *H. insolens* strain DSM 1800. The present invention further relates to isolated cutinase variants, as described herein, in which the variant is a variant of a parent cutinase, and the parent cutinase is encoded by a nucleic acid sequence which hybridizes under high, medium, or low stringency conditions with the nucleic acid sequence encoding the cutinase of *H. insolens* strain DSM 1800.

Nomenclature for Amino Acids and Alterations

The specification and claims refer to amino acids by their one-letter codes. A particular amino acid in a sequence is identified by its one-letter code and its position, e.g. Q1 indicates Gln (glutamine at position 1, i.e. at the N-terminal.

The nomenclature used herein for defining substitutions is basically as described in WO 92/05249. Thus, S11T indicates substitution of S (Ser) at position 11 with T (Thr). Q1C/L indicates substitution of Q (Gln) with C (Cys) or L (Leu).

Homology and Alignment

For purposes of the present invention, the degree of homology (or identity) may be suitably determined according to the method described in Needleman, S. B. and Wunsch, C. D., (1970), Journal of Molecular Biology, 48, 443–45, with the following settings for polypeptide sequence comparison: GAP creation penalty of 3.0 and GAP extension penalty of 0.1. The determination may be done by means of a computer program known such as GAP provided in the GCG program package (Program Manual for the Wisconsin Package, Version 8, August 1994, Genetics Computer Group, 575 Science Drive, Madison, Wis., USA 53711).

Two given sequences can be aligned according to the method described in Needleman (supra) using the same parameters. This may be done by means of the GAP program (supra).

*lens* cutinase (*H. insolens* cutinase numbering): Q1C/L, L2K/Q/V, A4V, G8D, S11T, N15D, A16T, T29C/I/M, V38H, N44D, S48E/K, H49Y, L66I, A88H/L/V, N91H, S116K, S119P, G120D, A130V, Q139R, T164S, T166M/I, L167P, I168F, I169A/G/T/V, L174F, I178V and/or R189A/H/V.

More specifically, the cutinase variant may include the following such substitutions or combinations of substitutions:

```
S48E + A88H + N91H + R189V
Q1L + L2K + G8D + N15D
N44D + A130V
Q1C + L2V + G120D
A88L + R189A
S48E + L66I + A88L + I169A + R189H
A88V + S116K + S119P + Q139R + I169V + R189V
A88V + R189A
S48K + A88H + I169G + R189H
Q1L + L2Q + A4V + S11T
T164S
L174F
H49Y
Q1L + L2K + G8D + N15D + S48E + A88H + N91H + R189V
Q1L + L2K + G8D + N15D + N44D + A130V
Q1L + L2K + G8D + N15D + S48E + A88H + N91H + A130V + R189V
G8D + N15D + A16T
A130V
Q1C + L2V
G8D + N15D + S48E + A88H + N91H + A130V + R189V
G8D + N15D + T29M + S48E + A88H + N91H + A130V + R189V
G8D + N15D + T29I + S48E + A88H + N91H + A130V + R189V
G8D + N15D + T29C + S48E + A88H + N91H + A130V + R189V
G8D + N15D + S48E + A88H + N91H + A130V + L174F + I178V + R189V
G8D + N15D + S48E + A88H + N91H + A130V + T166M + I168F + R189V
G8D + N15D + S48E + A88H + N91H + A130V + T166I + L167P + R189V
G8D + N15D + V38H + S48E + A88H + N91H + A130V + I169T + R189V
G8D + N15D + V38H + S48E + A88H + N91H + A130V + R189V
G8D + N15D + T29M + S48E + A88H + N91H + A130V + T166I + L167P + R189V
```

The homology between the parent cutinase and the cutinase variant may be above 80%, e.g. above 85% or above 90%, particularly above 95%.

Hybridization

Suitable experimental conditions for determining hybridization at low, medium, or high stringency between a nucleotide probe and a homologous DNA or RNA sequence involves presoaking of the filter containing the DNA fragments or RNA to hybridize in 5× SSC (Sodium chloride/Sodium citrate, Sambrook et al. 1989) for 10 min, and prehybridization of the filter in a solution of 5×SSC, 5× Denhardt's solution (Sambrook et al. 1989), 0.5% SDS and 100 μg/ml of denatured sonicated salmon sperm DNA (Sambrook et al. 1989), followed by hybridization in the same solution containing a random-primed (Feinberg, A. P. and Vogelstein, B. (1983) Anal. Biochem. 132:6–13), $^{32}$P-dCTP-labeled (specific activity>1×10$^9$ cpm/μg ) probe for 12 hours at ca. 45° C. The filter is then washed twice for 30 minutes in 2× SSC, 0.5% SDS at least *55° C. (low stringency), more preferably at least 60° C. (medium stringency), more preferably at least 65° C. (medium/high stringency), more preferably at least 70° C. (high stringency), even more preferably at least 75° C. (very high stringency).

Molecules to which the oligonucleotide probe hybridizes under these conditions are detected using an x-ray film.

Specific Substitutions

The variants may particularly comprise one or more substitutions corresponding to the following in the *H. inso-*

Optional Substitutions

In addition to the substitutions described above, the cutinase variant may optionally include one or more other amino acid alterations, particularly substitution of one or more amino acid residues corresponding to the following in the *H. insolens* cutinase (*H. insolens* cutinase numbering): Q1, L2, E6, E10, S11, A14, N15, F24, L46, E47, R51, D63, L138 and/or E179, more particularly one or more substitutions corresponding to Q1P, L2V, E6Q, E10Q, S11C, A14P, N15T, F24Y, L46I, E47K, R51P, D63N, L138I and/or E179Q.

More specifically, the cutinase variant may include the following such substitutions or combinations of substitutions:

R51P
E6N/Q+L138I
A14P+E47K
E47K
E179N/Q
E6N/Q+E47K+R51P
A14P+E47K+E179N/Q
E47K+E179N/Q
E47K+D63N
E6N/Q+E10N/Q+A14P+E47K+R51P+E179N/Q
E6N/Q+A14P+E47K+R51P+E179N/Q
Q1P+L2V+S11C+N15T+F24Y+L46I+E47K

Use of Cutinase Variant

The cutinase variant of the invention may be used, e.g., for the enzymatic hydrolysis of cyclic oligomers of poly (ethylene terephthalate), such as cyclic tri(ethylene terephthalate), abbreviated as c3ET.

In particular, this may be used to remove such cyclic oligomers from polyester containing fabric or yarn by treating the fabric or yarn with the cutinase variant, optionally followed by rinsing the fabric or yarn with an aqueous solution having a pH in the range of from about pH 7 to about pH 11. The treatment of polyester is conveniently carried out above the glass transition temperature of c3ET (about 55° C.) and below the glass transition temperature of polyester (about 70° C.). The process may be carried out in analogy with WO 97/27237.

The cutinase variant may be used to treat polyester-containing textile. e.g. PET (polymer of ethyleneglycol and terephthalic acid), P3GT (polymer of 1,3-propanediol and terephthalic acid) or a polyester/cotton blend. The treatment may provide benefits to the polyester textile such as improved wear and comfort, increased water permeability, reduced antistatic behavior, improve handle and softness, changed redeposition characteristics and/or color clarification.

The cutinase variant may be used to improve the functional finish of a PET-containing yarn or fabric by a treatment with the cutinase variant, followed by a treatment with a finishing agent such as a softener, an anti-crease resin, an anti-static agent, an anti-soiling agent or agents to impair wrinkle-free, permanent press ior fire resistance effects. The treatment with the cutinase variant may increase the number of functional groups in the surface, and this can be used to attach the functional finish. Examples of finishing agents are described in "SENSHOKU SIAGEKAKO BENRAN" published Oct. 15, 1998 by Nihon Seni Sentaa KK.

The cutinase variant of the invention is also useful in detergents, where it may be incorporated to improve the removal of fatty soiling, as described in WO 94/03578 and WO 94/14964. The addition of the cutinase variant to laundry detergent may reduce malodor from cloth which is accumulated during several wash/wear-cycles.

The cutinase variant may also be used for degradation and recycling of polyester such as polycaprolactone (PCL), poly-ethyleneglycol-terephthalate (PET), polylactic acid, polybutylenesuccinate, and poly(hydroxybutiric acid)-co-(hydroxyvaleric acid), e.g. film and bottles, e.g. as described in JP-A 5-344897.

The cutinase variant may also be used for other known applications of lipases and cutinases, for example, in the baking industry (e.g. as described in WO 94/04035 and EP 585988), in the papermaking industry (e.g. for pitch removal, see EP 374700), and in the leather, wool and related industries (e.g. for degreasing of animal hides, sheepskin or wool), and for other applications involving degreasing/defatting. It may be used in immobilized form in the fat and oil industry, as a catalyst in organic synthesis (e.g. esterification, transesterification or ester hydrolysis reactions).

Dyeing Polyester

The invention provides a process for dyeing polyester fabric or yarn. In this process, the fabric or yarn is first treated with a cutinase, e.g. 12–48 hours at 50–70° C. or 65–70° C., pH 7–10, followed by dyeing with dye, e.g. a reactive dye, a disperse dye or a cationic dye. The reactive dye may be one that reacts with OH or COOH groups, e.g. having the structure Chromophore-NHPh-$SO_2CH_2CH_2OSO_3Na$. The dyeing may be conducted at 40–80° C., e.g. for 20–60 minutes.

The cutinase may be a thermostable cutinase having a thermal denaturation temperature, $T_d$, at pH 8.5 which is at least 5° higher than the parent cutinase, e.g. 7–10° higher, e.g. a value of 65° C. or higher. The measurement may be made by DSC as described in an Example of this specification.

Surfactant

In the treatment of fabric or yarn, a conventional wetting agent and/or a dispersing agent may be used to improve the contact with the enzyme. The wetting agent may be a nonionic surfactant, e.g. an ethoxylated fatty alcohol. A very useful wetting agent is an ethoxylated and propoxylated fatty acid ester such as Berol 087 (product of Akzo Nobel, Sweden).

The dispersing agent may suitably be selected from nonionic, anionic, cationic, ampholytic or zwitterionic surfactants. More specifically, the dispersing agent may be selected from carboxymethylcellulose, hydroxypropylcellulose, alkyl aryl sulfonates, long-chain alcohol sulfates (primary and secondary alkyl sulfates), sulfonated olefins, sulfated monoglycerides, sulfated ethers, sulfosuccinates, sulfonated methyl ethers, alkane sulfonates, phosphate esters, alkyl isothionates, acylsarcosides, alkyltaurides, fluorosurfactants, fatty alcohol and alkylphenol condensates, fatty acid condensates, condensates of ethylene oxide with an amine, condensates of ethylene oxide with an amide, sucrose esters, sorbitan esters, alkyloamides, fatty amine oxides, ethoxylated monoamines, ethoxylated diamines, alcohol ethoxylate and mixtures thereof. A very useful dispersing agent is an alcohol ethoxylate such as Berol 08 (product of Akzo Nobel, Sweden).

Methods for Preparing Cutinase Variants

The cutinase variant of the invention can be prepared by methods known in the art, e.g. as described in WO 94/14963 or WO 94/14964 (Unilever). The following describes methods for the cloning of cutinase-encoding DNA sequences, followed by methods for generating mutations at specific sites within the cutinase-encoding sequence.

Cloning a DNA Sequence Encoding a Cutinase

The DNA sequence encoding a parent cutinase may be isolated from any cell or microorganism producing the cutinase in question, using various methods well known in the art. First, a genomic DNA and/or cDNA library should be constructed using chromosomal DNA or messenger RNA from the organism that produces the cutinase to be studied. Then, if the amino acid sequence of the cutinase is known, labeled oligonucleotide probes may be synthesized and used to identify cutinase-encoding clones from a genomic library prepared from the organism in question. Alternatively, a labeled oligonucleotide probe containing sequences homologous to another known cutinase gene could be used as a probe to identify cutinase-encoding clones, using hybridization and washing conditions of lower stringency.

Yet another method for identifying cutinase-encoding clones would involve inserting fragments of genomic DNA into an expression vector, such as a plasmid, transforming cutinase-negative bacteria with the resulting genomic DNA library, and then plating the transformed bacteria onto agar containing a substrate for cutinase (i.e. maltose), thereby allowing clones expressing the cutinase to be identified.

Alternatively, the DNA sequence encoding the enzyme may be prepared synthetically by established standard methods, e.g. the phosphoroamidite method described S. L. Beaucage and M. H. Caruthers, (1981), Tetrahedron Letters 22, p. 1859–1869, or the method described by Matthes et al., (1984), EMBO J. 3, p. 801–805. In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., (1988), Science 239, 1988, pp. 487–491.

Construction of Cutinase Variant

A cutinase variant may be obtained by site-directed mutagenesis at selected positions or by localized random mutagenesis, i.e. by introduction of random amino acid residues in selected positions or regions of the parent enzyme, e.g. as described in WO 95/22615. A preferred method is to use doped or spiked oligonucleotides for the mutagenesis.

The selected positions may be one more of those described above, and the selected region may be one comprising one or more of these positions. Some particular examples are:

| A. Spiked oligo shuffling: | |
|---|---|
| Library S1: | 44, 46, 48, 51, 55 |
| Library S2: | 48, 66, 88, 91, 119, 169, 189 |
| Library S3: | 26, 66, 70, 139, 167, 168, 169, 174 |
| Library S4: | 4, 5, 6, 33, 34 |
| Library S5: | 6, 7, 8, 9, 55, 56, 57 |

| B. Doped libraries: | |
|---|---|
| Library 1: | 42–52 |
| Library 2: | 59–77 |
| Library 3: | 116–122 |
| Library 4: | 1–16 |
| Library 5: | 69, 70, 73 |
| Library 6: | 140–145 |
| Library 7: | 161, 162, 164–174 |

Site-Directed Mutagenesis

Once a cutinase-encoding DNA sequence has been isolated, and desirable sites for mutation identified, mutations may be introduced using synthetic oligonucleotides. These oligonucleotides contain nucleotide sequences flanking the desired mutation sites. In a specific method, a single-stranded gap of DNA, the cutinase-encoding sequence, is created in a vector carrying the cutinase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984), Biotechnology 2, p. 646–639. U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into cutinase-encoding DNA sequences is described in Nelson and Long, (1989), Analytical Biochemistry 180, p. 147–151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Expression of Cutinase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

Expression Vector

The recombinant expression vector carrying the DNA sequence encoding a cutinase variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. Examples of suitable expression vectors include pMT838.

Promoter

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell.

Examples of suitable promoters for directing the transcription of the DNA sequence encoding a cutinase variant of the invention, especially in a bacterial host, are the promoter of the lac operon of *E.coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, the TPI (triose phosphate isomerase) promoter from *S. cerevisiae* (Alber et al. (1982), J. Mol. Appl. Genet 1, p. 419–434, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

Expression Vector

The expression vector of the invention may also comprise a suitable transcription terminator and, in eukaryotes, polyadenylation sequences operably connected to the DNA sequence encoding the α-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a cutinase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

Host Cells

The cell of the invention, either comprising a DNA construct or an expression vector of the invention as defined above, is advantageously used as a host cell in the recombinant production of a cutinase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, particularly a microbial cell, e.g. a bacterial or a fungal (including yeast) cell.

Examples of suitable bacteria are Gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gramnegative bacteria such as *E.coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae.*

The host cell may also be a filamentous fungus e.g. a strain belonging to a species of *Aspergillus*, particularly *Aspergillus oryzae* or *Aspergillus niger*, or a strain of *Fusarium*, such as a strain of *Fusarium oxysporum, Fusarium graminearum* (in the perfect state named *Gibberella zeae*, previously *Sphaeria zeae*, synonym with *Gibberella roseum* and *Gibberella roseum* f. sp. *cerealis*), or *Fusarium sulphureum* (in the prefect state named *Gibberella puricaris*, synonym with *Fusarium trichothecioides, Fusarium bactridioides, Fusarium sambucinum, Fusarium roseum,* and *Fusarium roseum* var. *graminearum*), *Fusarium cerealis* (synonym with *Fusarium crokkwellense*), or *Fusarium venenatum.*

In a particular embodiment of the invention the host cell is a protease deficient or protease minus strain.

This may for instance be the protease deficient strain *Aspergillus oryzae* JaL 125 having the alkaline protease gene named "alp" deleted. This strain is described in WO 97/35956 (Novo Nordisk).

Filamentous fungi cells may be transformed by a process involving protoplast formation and transformation of the protoplasts followed by regeneration of the cell wall in a manner known per se. The use of *Aspergillus* as a host micro-organism is described in EP 238 023 (Novo Nordisk A/S), the contents of which are hereby incorporated by reference.

Production of Cutinase Variant by Cultivation of Transformant

The invention relates, inter alia, to a method of producing a cutinase variant of the invention, which method comprises cultivating a host cell under conditions conducive to the production of the variant and recovering the variant from the cells and/or culture medium.

The medium used to cultivate the cells may be any conventional medium suitable for growing the host cell in question and obtaining expression of the cutinase variant of the invention. Suitable media are available from commercial suppliers or may be prepared according to published recipes (e.g. as described in catalogues of the American Type Culture Collection).

The cutinase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Expression of Variant in Plants

The present invention also relates to a transgenic plant, plant part or plant cell which has been transformed with a DNA sequence encoding the variant of the invention so as to express and produce this enzyme in recoverable quantities. The enzyme may be recovered from the plant or plant part. Alternatively, the plant or plant part containing the recombinant enzyme may be used as such.

The transgenic plant can be dicotyledonous or monocotyledonous, for short a dicot or a monocot. Examples of monocot plants are grasses, such as meadow grass (blue grass, Poa), forage grass such as festuca, lolium, temperate grass, such as Agrostis, and cereals, e.g. wheat, oats, rye, barley, rice, sorghum and maize (corn).

Examples of dicot plants are tobacco, legumes, such as lupins, potato, sugar beet, pea, bean and soybean, and cruciferous (family Brassicaceae), such as cauliflower, oil seed rape and the closely related model organism *Arabidopsis thaliana.*

Examples of plant parts are stem, callus, leaves, root, fruits, seeds, and tubers. In the present context, also specific plant tissues, such as chloroplast, apoplast, mitochondria, vacuole, peroxisomes and cytoplasm are considered to be a plant part. Furthermore, any plant cell, whatever the tissue origin, is considered to be a plant part.

Also included within the scope of the invention are the progeny of such plants, plant parts and plant cells.

The transgenic plant or plant cell expressing the variant of the invention may be constructed in accordance with methods known in the art. In short the plant or plant cell is constructed by incorporating one or more expression constructs encoding the enzyme of the invention into the plant host genome and propagating the resulting modified plant or plant cell into a transgenic plant or plant cell.

Conveniently, the expression construct is a DNA construct which comprises a gene encoding the enzyme of the invention in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, e.g. on the basis of when, where and how the enzyme is desired to be expressed. For instance, the expression of the gene encoding the enzyme of the invention may be constitutive or inducible, or may be developmental, stage or tissue specific, and the gene product may be targeted to a specific tissue or plant part such as seeds or leaves. Regulatory sequences are e.g. described by Tague et al, Plant, Phys., 86, 506, 1988.

For constitutive expression the 35S-CaMV promoter may be used (Franck et al., 1980. Cell 21: 285–294). Organ-specific promoters may eg be a promoter from storage sink tissues such as seeds, potato tubers, and fruits (Edwards & Coruzzi, 1990. Annu. Rev. Genet. 24: 275–303), or from metabolic sink tissues such as meristems (Ito et al., 1994. Plant Mol. Biol. 24: 863–878), a seed specific promoter such as the glutelin, prolamin, globulin or albumin promoter from rice (Wu et al., Plant and Cell Physiology Vol. 39, No. 8 pp. 885–889 (1998)), a Vicia faba promoter from the legumin B4 and the unknown seed protein gene from Vicia faba described by Conrad U. et al, Journal of Plant Physiology Vol. 152, No. 6 pp. 708–711 (1998), a promotter from a seed oil body protein (Chen et al., Plant and cell physiology vol. 39, No. 9 pp. 935–941 (1998), the storage protein napA promoter from *Brassica napus*, or any other seed specific promoter known in the art, eg as described in WO 91/14772. Furthermore, the promoter may be a leaf specific promoter such as the rbcs promoter from rice or tomato (Kyo-zuka et al., Plant Physiology Vol. 102, No. 3 pp. 991–1000 (1993), the chlorella virus adenine methyltransferase gene promoter (Mitra, A. and Higgins, D W, Plant Molecular Biology Vol. 26, No. 1 pp. 85–93 (1994), or the aldP gene promoter from rice (Kagaya et al., Molecular and General Genetics Vol. 248, No. 6 pp. 668–674 (1995), or a wound inducible promoter such as the potato pin2 promoter (Xu et al, Plant Molecular Biology Vol. 22, No. 4 pp. 573–588 (1993).

A promoter enhancer element may be used to achieve higher expression of the enzyme in the plant. For instance, the promoter enhancer element may be an intron which is placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including *Agrobacterium*-mediated transformation, virus-mediated transformation, micro injection, particle bombardment, biolistic transformation, and electroporation (Gasser et al, Science, 244, 1293; Potrykus, Bio/Techn. 8, 535, 1990; Shimamoto et al, Nature, 338, 274, 1989).

Presently, *Agrobacterium tumefaciens* mediated gene transfer is the method of choice for generating transgenic dicots (for review Hooykas & Schilperoort, 1992. Plant Mol. Biol. 19: 15–38), however it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992. Plant J. 2: 275–281; Shimamoto, 1994. Curr. Opin. Biotechnol. 5: 158–162; Vasil et al., 1992. Bio/Technology 10: 667–674). An alternative method for transformation of monocots is based on protoplast transformation as described by Omirulleh S, et al., Plant Molecular biology Vol. 21, No. 3 pp. 415–428 (1993).

Following transformation, the transformants having incorporated the expression construct are selected and regenerated into whole plants according to methods well-known in the art.

MATERIALS AND METHODS

Strains and Plasmids

*E.coli* DH12S (available from Gibco BRL) is used for yeast plasmid rescue.

*E.coli* JM110 (available from Toyobo K.K., Japan) is used for preparing recombinant plasmids.

pJSO026 is a *S. cerevisiae* expression plasmid described in WO 97/07205 and in J. S. Okkels, (1996) "A URA3-promoter deletion in a pYES vector increases the expression level of a fungal lipase in Saccharomyces cerevisiae. Recombinant DNA Bio-technology III: The Integration of Biological and Engineering Sciences, vol. 782 of the Annals of the New York Academy of Sciences).

pJC039 is a yeast and *E.coli* shuttle vector for expression of the "reference" cutinase variant described in the Examples under the control of TPI promoter, constructed from pJSO026.

*Saccharomyces cerevisiae* YNG318: MATa Dpep4[cir+] ura3-52, leu2-D2, his 4-539 is used for the construction of yeast library and the expression of *H. insolens* cutinase. It is described in J. Biol. Chem. 272 (15), 9720–9727, 1997.

Media and Substrates

| SC-glucose | |
|---|---|
| 100 ml/L | 20% glucose |
| 4 ml/L | 5% threonine |
| 10 ml/L | 1% tryptophan |
| 25 ml/L | 20% casamino acids |
| 100 ml/L | 10 × basal solution |
| | Filter sterilized separately |

| 10 × Basal solution | |
|---|---|
| 66.8 g/L | yeast nitrogen base w/o amino acids |
| 100 g/L | succinate |
| 60 g/L | NaOH |

| YPD | |
|---|---|
| 20 g/L | Bacto pepton |
| 10 g/L | yeast extract |
| 100 ml/L | 20% glucose (sterilized separately) |

BETEB

Terephthalic acid bis(2-hydroxyethyl)ester dibenzoate is herein abbreviated as BETEB (benzoyl-ethylene-terephthalic-ethelene-benzoate). It was prepared from terephthalic acid bis (2-hydroxyethyl) ester and benzoic acid.

| BETEB plate | |
|---|---|
| 100 ml/l | 500 mM glycine buffer (pH 8.5) |
| 1 g/l | BETEB (soluble in ethanol) |
| 30 g/l | agar |

| PEG/LiAc solution | |
|---|---|
| 50 ml | 40% PEG4000 (sterile) |
| 1 ml | 5 M LiAc (sterile) |

Nucleotide Mixture for Dop83-2 (SEQ ID NO: 5):
1 (nucleotide 25): G 91%, A 9%
2 (nucleotide 26): G 96%, C 4%
3 (nucleotide 37): G 92.5%, A 7.5%
4 (nucleotide 38): A 96%, C 4%
5 (nucleotide 39): G 0.5%, A 3.5%, T 96%
6 (nucleotide 40): G 96%, A 2%, T 2%
7 (nucleotide 41): A 4.5%, C 95.5%
8 (nucleotide 42): A 2.5%, T 97.5%
9 (nucleotide 43): G 92%, A 2.5%, T 3%, C 2.5%
10 (nucleotide 45): G 71.5%, A 1%, T 27.5%
11 (nucleotide 46): G 3.5%, A 2%, T 43%, C 51.5%
12 (nucleotide 47): T 93.5%, C 6.5%
13 (nucleotide 49): G 92%, A 2.5%, T 3%, C 2.5%
14 (nucleotide 51): G 71.5%, T 27.5%, A 1%
15 (nucleotide 52): A 98%, C 2%
16 (nucleotide 53): G 2.5%, T 4.5%, C 93%
17 (nucleotide 54): G 54.5%, A 9.5%, T 36%
18 (nucleotide 58): G 2%, A 3.5%, T 94.5%
19 (nucleotide 59): A 4%, T 91%, C 5%
20 (nucleotide 61): G 4.5%, T 95.5%
21 (nucleotide 62): T 95.5%, C 4.5%
22 (nucleotide 63): G 98%, A 2%

Methods

Lipase Activity (LU)

A substrate for lipase is prepared by emulsifying tributyrin (glycerin tributyrate) using gum Arabic as emulsifier. The hydrolysis of tributyrin at 30° C. at pH 7 is followed in a pH-stat titration experiment. One unit of lipase activity (1 LU) equals the amount of enzyme capable of releasing 1 μmol butyric acid/min at the standard conditions.

Primary Screening Method

1. Spread yeast library onto SC-glucose plates and incubate for 3 days at 30° C.
2. Replica to new SC-glucose plates with nitrate filters by using velvet cloth. Incubate the plates at 30° C. for 1 days. (or 20° C. O/W)
3. Transfer the filters to pre-heated 0.1% BETEB plates (pH 8.5) with/without 50 ppm Avolan.
4. Incubate BETEB plate with Avolan at 70° C. and w/o Avolan at 73° C. O/N.
5. Remove the filters and find the yeast clones with clear zones.
6. Isolate candidate clones from the master plate and inoculate to a new SC-glucose plate and 1 ml of YPD medium in 24 well plates.

Secondary Screening Method

1. Cultivate YPD medium in 24 well plates at 30° C. for 2 days at 180 rpm.
2. Centrifuge the plate/or just leave them still for a few hours.
3. Apply 5 μl and 10 μl of supernatants to holes in a BETEB plates with Avolan and 2 without Avolan.
4. Incubate one BETEB plate and the BETEB plate with Avolan at 60° C., the other BETEB plate at 68° C. overnight.
5. Check the diameter of clear zones.
6. Determine the LU activity of the supernatant of the clones which retains activity at 68° C. or 60° C. with Avolan.
7. Adjust the LU activity to 10 LU/ml and apply to BETEB plates as 4).
8. Check the diameter of clear zones.

Method for Construction of Yeast Library

1. Mix 0.5 μl of vector (Hind III-Xba I digested) and 1 μl of PCR fragments.
2. Thaw YNG318 competent cell on ice.
3. Mix 100 μl of the cell, the DNA mixture and 10 μl of carrier DNA (Clontech) in Falcon 1058.
4. Add 0.6 ml PEG/LiAc solution and mix gently.
5. Incubate at 30° C. at 200 rpm for 30 min.
6. Incubate at 42° C. for 15 min (heat shock).
7. Transfer to a eppendorf tube and centrifuge for 5 sec.
8. Remove the supernatant and resolve in 3 ml of YPD.
9. Incubate the cell suspension for 45 min at 30 rpm at 30° C.
10. Pour the suspension to SC-glucose plates to give ca. 300 clones/plate.

Library Construction

Dop libraries are constructed by SOE method followed by yeast recombination.

Other methods

E.coli transformation for constructing libraries and subcloning is carried out by electroporation (BIO-RAD Gene Pulser).

DNA Plasmids are prepared by alkaline method (Molecular Cloning, Cold Spring Harbor) or with the Qiagen® Plasmid Kit.

DNA fragments are recovered from agarose gel by the Qiagen gel extraction Kit.

PCR is carried out by the PTC-200 DNA Engine

The ABI PRISM™ 310 Genetic Analyzer is used for determination of all DNA sequences.

Yeast transformation is carried out by lithium acetate method.

Yeast total DNA is extracted by the Robzyk and Kassir's method described in Nucleic acids research vol. 20, No 14 (1992) 3790.

All positive clones in the secondary assay are cultivated in 1 ml of YPD at 30° C. overnight for extracting total yeast DNA. The prepared DNA is introduced into E.coli, isolate E.coli colonies and prepare their plasmids for sequencing and further evaluation.

EXAMPLES

Example 1

Construction of Cutinase Variants by Doping

The first PCR reaction was carried out with 2 primer pairs, 620AM34 (SEQ ID NO: 3) and Dop2-R (SEQ ID NO: 4), and Dop83-2 (SEQ ID NO: 5 with nucleotide mixtures described above) and 680AM35 (SEQ ID NO: 6) under the following condition:

| | |
|---|---|
| 48.6 μl | H₂O |
| 33 μl | 3.3 × reaction buffer |
| 4.4 μl | 25 mM MgOAc |
| 2 μl | rTth polymerase (perkin |

| | | |
|---|---|---|
| 8 μl | Elmer) 10 mM dNTPs | |
| 1 μl × 2 | 100 pmol/μl Primers | |
| 1 μl | 0.5 μg/μl Template (pJC039) | |

| | | |
|---|---|---|
| 1 | 94° C. | 20 sec |
| 2 | 94° C. | 15 sec |
| 3 | 45° C. | 45 sec |
| 4 | 72° C. | 30 sec + 3 sec/cycle |
| 2–4 | | 50 cycles |
| 5 | 72° C. | 10 min |

The resulting fragments were gel-purified and used for the template for the second PCR reaction. The second PCR was carried out with 620 (SEQ ID NO: 7) and 680 (SEQ ID NO: 8) as primers under the following condition.

| | | |
|---|---|---|
| 38.2 μl | H₂O | |
| 5 μl | 10 × reaction buffer | |
| 1 μl | Klen Taq LA (CLONTECH) | |
| 4 μl | 10 mM dNTPs | |
| 0.4 μl × 2 | 100 pmol/μl Primers | |
| 0.5 μl × 2 | PCR fragments | |

| | | |
|---|---|---|
| 1 | 98° C. | 10 sec |
| 2 | 68° C. | 90 sec |
| 1–2 | | 30 cycles |
| 3 | 68° C. | 10 min |

Spiked Oligo Shuffling Library

Spiked libraries were constructed as follows:

PCR reaction for preparing a gene fragment of the reference variant described in a later example was carried out with rTth polymerase and AM34 (SEQ ID NO: 9) and AM35 (SEQ ID NO: 10) as primers as described above and the fragment was gel-purified.

About 10 μg DNA/250 μl was incubated with 0.8 μl DNaseI (Gibco BRL 18068-015) and 30 μl 10× buffer at 25° C. for 7–10min. Adding EDTA to the final concentration at 10 mM stopped the reaction.

DNA fragments of correct size (50–150 bp) was purified by Whatman glass filter.

Then the DNase treated fragments were reassembled under the following condition.

| | |
|---|---|
| 0.2, 0.5 and 1 pmol | DNase-treated template |
| 3, 6, 12 × molar | excess of each mutagenic oligo |
| 1 beads | Ready-to-go |
| 0.1 μl | Pwo polymerase |
| final volume 25 μl | |

| | |
|---|---|
| 0.2, 0.5, 1 and 2 μl | 1st PCR reaction |
| 2 beads | Ready-to-go |
| 0.3 μl | 100 pmol primer 1 (AM34, SEQ ID NO: 9) |
| 0.3 μl | 100 pmol primer 2 (AM35, SEQ ID NO: 10) |
| 0.1 μl | Pwo polymerase |

Using the above PCR mixture as a template, second PCR was carried out under following condition:

| | | |
|---|---|---|
| 1 | 94° C. | 2 min. |
| 2 | 94° C. | 30 sec |
| 3 | 45° C. | 30 sec |
| 4 | 72° C. | 1 min. |
| 2–4 | | 30 cycles |
| 5 | 72° C. | 5 min. |

| | | |
|---|---|---|
| 1 | 94° C. | 2 min. |
| 2 | 94° C. | 30 sec |
| 3 | 55° C. | 30 sec |
| 4 | 72° C. | 90 sec |
| 2–4 | | 25 cycles |
| 5 | 72° C. | 10 min. |

Example 2

Thermostability of Variants

A number of samples were prepared, each containing 10 LU/ml of a variant of the *H. insolens* cutinase. 20 μl of each sample was applied to a well of a BETEB plate, and the plate was incubated at 68° overnight (14 hours). The presence of a clearing zone around the well was taken as a positive result.

The following variants according to the invention were tested, and a reference variant (not according to the invention) was included for comparison.

| | |
|---|---|
| Reference | E6Q +A14P +E47K +R51P +E179Q |
| Invention | Reference +S48E +A88H +N91H +R189V |
| | Reference +(AAVDSNHTPAVPELVAR, SEQ ID NO: 2) +Q1L +L2K +G8D +N15D |
| | Reference +N44D +A130V |
| | Reference +Q1C +L2V +G120D |
| | Reference +A88L +R189A |
| | Reference +S48E +L66I +A88L +I169A +R189H |
| | Reference +A88V +S116K +S119P +Q139R +I169V +R189V |
| | Reference +A88V +R189A |
| | Reference +S48K +A88H +I169G +R189H |
| | Reference +Q1L +L2Q +A4V +S11T |
| | Reference +T164S |
| | Reference +L174F |
| | Reference +H49Y |
| | Reference +(AAVDSNHTPAVPELVAR, SEQ ID NO: 2) +Q1L +L2K +G8D +N15D +S48E +A88H +N91H +R189V |
| | Reference +(AAVDSNHTPAVPELVAR, SEQ ID NO: 2) +Q1L +L2K +G8D +N15D +N44D +A130V |
| | Reference +(AAVDSNHTPAVPELVAR, SEQ ID NO: 2) +Q1L +L2K +G8D +N15D +N44D +S48E +A88H +N91H +A130V +R189V |
| | Reference +G8D +N15D +A16T |
| | Reference +A130V |

-continued

Reference +Q1C +L2V
Reference +G8D +N15D +S48E +A88H +N91H +A130V +R189V
Reference +G8D +N15D +T29M +S48E +A88H +N91H +A130V +R189V
Reference +G8D +N15D +T29I +S48E +A88H +N91H +A130V +R189V
Reference +G8D +N15D +T29C +S48E +A88H +N91H +A130V +R189V
Reference +G8D +N15D +S48E +A88H +N91H +A130V +L174F +I178V +R189V
Reference +G8D +N15D +S48E +A88H +N91H +A130V +T166M +I168F +R189V
Reference +G8D +N15D +S48E +A88H +N91H +A130V +T166I +L167P +R189V
Reference +G8D +N15D +V38H +S48E +A88H +N91H +A130V +I169T +R189V
Reference +G8D +N15D +V38H +S48E +A88H +N91H +A130V +R189V
Reference +G8D +N15D +T29M +S48E +A88H +N91H +A130V +T166I +L167P +R189V As indicated above, each variant contained the same substitutions as the reference variant (E6Q+A14P+E47K+R51P+E179Q) and additionally one or more substitutions according to the invention. As shown above, four variants are believed to have an N-terminal extension stemming from the substitution A(−7)V in the prosequence resulting in an alteration of the cleavage site.

The results were that all variants of the invention showed a distinct clearing zone whereas the reference did not. The reference variant showed a clearing zone in a similar experiment at 60° C. Thus, each set of substitutions according to the invention markedly improved the thermostability of the variant.

Some variants were also tested at higher temperatures, and some of the above variants gave positive results at temperatures as high as 76° C.

Example 3

Stability of Variants in Presence of Detergent

Cutinase variants were incubated with anionic surfactant (10 or 40 ppm of Avolan, product of Bayer) at 60° C., and the residual activity was determined after 14 hours. 8 of the variants described in the previous example were found to have significant residual activity after incuation with 10 ppm of detergent and some activity with 40 ppm. The reference variant showed no residual activity.

Example 4

Thermostability by DSC

Thermostability of cutinase variants was investigated by means of Differential Scanning Calorimetry (DSC) at pH 10 (50 mM glycine buffer). The thermal denaturation temperature, Td, was taken as the top of denaturation peak (major endo-thermic peak) in thermograms (Cp vs. T) obtained after heating of enzyme solutions at a constant programmed heating rate.

The reference variant described above was found to have Td of 68° C. Three variants according to the invention described in Example 2 were found to have Td of 71–72° C., i.e. a clear improvement.

Example 5

Washing Performance of Variant

The reference variant and one variant of the invention described in Example 2 were tested in washing tests with two different detergents at the following conditions:

Detergent: Commercial Japanese detergents, rich in anionic surfactant
Detergent concentration: 0.50 g/L or 0.67 g/L
Test swatches per beaker:
3 cotton swatches (8×8 cm) soiled with lard/fat brown
3 cotton/polyester swatches (4.5×4.5 cm) soiled with lipstick (20 LS)
2 commercial sebum swatches (5×5 cm)
1 white polyester swatch (5×5 cm)
Washing machine: Terg-O-Tometer, 100 r.p.m.
Dosage of cutinase variant: 0, 2000, 5000, 10000 LU/L
Water hardness: 3° dH (Ca)
Washing temperature: 25° C.
Washing liquor: 1 Liter/beaker
Washing time: 10 min
Rinse: 10 min in running tap water
Drying: line dry, overnight The detergency was determined by measuring remisssion increase ($\Delta R$) for the lipstick swatches compared to swatches washed without addition of cutinase variant. The results showed that at dosages of 2000–10000 LU/L with each detergent, the cutinase variant of the invention provided $\Delta R$ of 10–16 whereas the reference variant provided $\Delta R$ of 3–7.

Redeposition of fat brown from lard swatches was determined by measuring remission increase ($\Delta R$) for the white polyester swatches compared to swatches washed without addition of cutinase variant. The results showed that at a dosage of 5000–10000 LU/L with each detergent, the cutinase variant of the invention provided $\Delta R$ of more than twice of that provided by the reference variant.

Further, the stability of the two variants was determined in solutions of the two detergents. After 10 minutes at 25° C., the variant of the invention showed 92–95% residual activity in the two detergents, whereas the reference variant showed 71–72% residual activity. The results showed that the variant of the invention provides a clearly improved washing performance in terms of washing performance, anti-redeposition effect and stability in detergent solution.

Example 6

Treatment of Polyester Textile

Polyester textile was treated with a cutinase variant of the invention and with the reference variant (both described in Example 2) as follows:
1. Test Conditions
  Temp.: 75° C.
  Washing time: 3 hrs
  pH: 9.0 (50 mM Glycylglycine buffer)
  Textile: Polyester (Teijin), 14 cm×14 cm
  Bath ratio: 5 pieces/1000 ml (=around 13 g/L)
  Dosage of enzyme: 0, 10, 50, 100 mg/L (based on enzyme protein)
  T-O-M: 100 rpm
  Rinsing time: 10 min by tap water
2. Procedure
  1. Dried a set of five pieces polyester at 105° C. for 2 hrs
  2. Cool them in a desiccator for at least 30 min
  3. Weighted out the set
  4. Washed the set of Polyester by the variant at 75° C. for 3 hrs at 100 rpm
  5. Rinsed the set for 10 min by tap water
  6. Line dried them overnight
  7. Dried them at 105° C. for 2 hrs
  8. Cool them in a desiccator for at least 30 min 9. Weighted out the set
10. Calculated weight loss The results are shown below as weight loss.

| | Dosage | | | |
|---|---|---|---|---|
| Variant | 0 mg/L | 10 mg/L | 50 mg/L | 100 mg/L |
| Invention | 0.05% | 0.95% | 1.44% | 1.44% |
| Reference | 0.05% | 0.33% | 0.43% | 0.20% |

The results show that the variant of the invention is sufficiently thermostable to act at 75° C., but the reference variant has little effect.

Example 7

Cleaning Effect on Denatured Cooking Oil

A cutinase variant of the invention (described in Example 2) was tested for its cleaning effect on real oxidized oil stain from kitchen.

The cutinase variant was added in an amount of 1000 LU/ml to a commercial liquid dish-washing detergent with neutral pH. The detergent with the cutinase variant was applied directly to denatured cooking oil stuck on ventilator filter from kitchen, it was left for 15, 30 or 60 minutes, and was finally rinsed with tap water for 1 minute.

Visual inspection showed that the oxidized oil was effectively removed. A control experiment using the same detergent without enzyme showed little effect.

Example 8

Anti-Pilling and Depilling Effects of Cutinase Variant

Polyester textile was treated with a cutinase variant of the invention (described in Example 2) and, as control, with the reference variant of Example 2. The conditions were: 75° C., 3 ours washing, pH 9.0 (glycylglycine buffer), 14×14 cm peach skin polyester (produced by Toray, Japan), bath ratio 5 pieces (around 16 g) per 1000 ml, Tergotometer at 100 rpm, followed by 10 min rinsing in tap water.

Textile treated with 10, 50 and 100 mg/l of the cutinase variant showed improved de-pilling and anti-pilling compared to the control. It was observed that the yarn network became more visible by the treatment, apparently because fuzz was removed and the fuzz (microfibrils) became shorter.

Example 9

Effect of Cutinase Variant on Water Absorption

Tropical plain-weave polyester (Teijin, Japan) was treated with 100 mg/l of the same cutinase variant and at the same conditions as in the previous example, followed by a treatment with a protease (Alcalase®) to remove any cutinase protein remaining on the surface of the fabric, soaping, rinsing and drying. A control was made in the same way without the cutinase variant treatment.

The treated textile was tested by cutting into strips, dipping the end of the strips into a colorant solution, removing excess colorant, and measuring the height of the colored part. The treatment with the cutinase variant increased the height of the colored part from 16 to 77 mm, indicating an improved water absorption.

What is claimed is:

1. A cutinase variant, wherein the cutinase variant has above 90% homology to SEQ ID NO:1 and comprises a substitution of at least one amino acid residue corresponding to position A4, T29, A88, N91, A130, Q139, I169, I178 or R189 in SEQ ID NO:1; and wherein the cutinase variant has cutinase activity.

2. The cutinase variant claim 1, which comprises the substitution A4V, T29M/I/C, A88H/L/V, N91H, A130V, Q139R, I169A/G/T/V, I178V or R189A/H/V.

3. The cutinase variant of claim 1, wherein the cutinase variant is a variant of the cutinase from Humicola insolens strain DSM 1800.

4. The cutinase variant of claim 1, wherein the cutinase variant has above 95% homology to SEQ ID NO:1.

5. The cutinase variant of claim 1, which cutinase variant further comprises at least one amino acid substitution at a position corresponding to position Q1, L2, E6, G8, E10, S11, A14, N15, A16, F24, V38, N44, L46, E47, S48, H49, R51, D63, L66, S116, S119, G120, L138, T164, T166, L167, I168, L174 or E179 in SEQ ID NO:1.

6. The cutinase variant of claim 1, which cutinase variant further comprises at least one amino acid substitution at a position corresponding to Q1P/C/L, L2K/Q/V, E6Q, G8D, E10Q, S11C/T, A14P, N15T/D, A16T, F24Y, V38H, N44D, L46I, E47K, S48E/K, H49Y, R51P, D63N, L66I, S116K, S119P, G120D, L138I, T164S, T166M/I, L167P, I168F, L174F or E179Q in SEQ ID NO:1.

7. The cutinase variant of claim 1, which cutinase variant further comprises substitutions corresponding to E6Q+ A14P+E47K+R51P+E179Q in SEQ ID NO:1.

8. The cutinase variant of claim 1, which cutinase variant has hydrolytic activity towards terephthalic acid esters.

9. The cutinase variant of claim 1, which cutinase variant has hydrolytic activity towards cyclic tri(ethylene terephthalate) and/or Terephthalic acid bis(2-hydroxyethyl) ester dibenzoate.

10. The cutinase variant of claim 6, comprising substitutions corresponding to E6Q+A14P+E47K+R51P+E179Q in SEQ ID NO:1.

11. The cutinase variant of claim 1, wherein the cutinase variant is a variant of a cutinase that has the amino acid sequence of SEQ ID NO:1 and wherein the cutinase variant comprises the substitutions corresponding to E6Q+A14P+E47K+R51P+A130V+E179Q in SEQ ID NO:1.

12. The cutinase variant of claim 1, wherein the cutinase variant comprises a substitution at a position corresponding to A4.

13. The cutinase variant of claim 1, wherein the cutinase variant comprises a substitution at a position corresponding to T29.

14. The cutinase variant of claim 1, wherein the cutinase variant comprises a substitution at a position corresponding to A88.

15. The cutinase variant of claim 1, wherein the cutinase variant comprises a substitution at a position corresponding to N91.

16. The cutinase variant of claim 1, wherein the cutinase variant comprises a substitution at a position corresponding to A130.

17. The cutinase variant of claim 1, wherein the cutinase variant comprises a substitution at a position corresponding to Q139.

18. The cutinase variant of claim 1, wherein the cutinase variant comprises a substitution at a position corresponding to I169.

19. The cutinase variant of claim 1, wherein the cutinase variant comprises a substitution at a position corresponding to I178.

20. The cutinase variant of claim 1, wherein the cutinase variant comprises a substitution at a position corresponding to R189.

21. A cutinase variant, wherein the cutinase variant differs from SEQ ID NO:1 by 1 to 20 substitutions and comprises a substitution of at least one amino acid residue corresponding to position A4, T29, A88, N91, A130, Q139, I169, I178 or R189 in SEQ ID NO:1; and wherein the cutinase variant has cutinase activity.

22. A cutinase variant, wherein the cutinase variant has above 90% homology to SEQ ID NO:1 and comprises a substitution or substitutions selected from the following group of substitutions in SEQ ID NO:1;

S48E+A88H+N91H+R189V;
N44D+A130V;
A88L+R189A;
S48E+L66I+A88L+I169A+R189H;
A88V+S116K +S119P+Q139R+I169V+R189V;
A88V+R189A;
S48K+A88H+I169G+R189H;
Q1L+L2Q+A4V+S11T;
L174F;
Q1L+L2K+G8D+N15D+S48E+A88H+N91H+R189V;
Q1L+L2K+G8D+N15D+N44D+A130V;
Q1L+L2K+G8D+N15D+S48E+A88H+N91H+A130V+R189V;
A130V;
G8D+N15D+S48E+A88H+N91H+A130V+R189V;
G8D+N15D+T29M+S48E+A88H+N91H+A130V+R189V;
G8D+N15D+T29I+S48E+A88H+N91H+A130V+R189V;
G8D+N15D+T29C+S48E+A88H+N91H+A130V+R189V;
G8D+N15D+S48E+A88H+N91H+A130V+L174F+I178V+R189V;
G8D+N15D+S48E+A88H+N91H+A130V+T166M+I168F+R189V;
G8D+N15D+S48E+A88H+N91H+A130V+T166I+L167P+R189V;
G8D+N15D+V38H+S48E+A88H+N91H+A130V+I169T+R189V;
G8D+N15D+V38H+S48E+A88H+N91H+A130V+R189V; and
G8D+N15D+T29M+S48E+A88H+N91H+A130V+T166I+L167P+R189V;
and wherein the variant has cutinase activity.

23. The cutinase variant of claim 22, wherein the cutinase variant is a variant of the cutinase from *Humicola insolens* strain DSM 1800.

24. The cutinase variant of claim 22, wherein the cutinase variant has above 95% homology to SEQ ID NO:1.

25. The cutinase variant of claim 22, further comprising substitutions corresponding to E6Q+A14P+E47K+R51P+E179Q in SEQ ID NO:1.

26. The cutinase variant of claim 2, further comprising substitutions corresponding to E6Q+A14P+E47K+R51P+E179Q in SEQ ID NO:1.

27. The cutinase variant of claim 1, wherein the cutinase variant comprises the following substitutions E6Q, G8D, A14P, N15D, E47K, S48E, R51P, A88H, N91H, A130V, E179Q and R189V.

28. The cutinase variant of claim 3, wherein the cutinase variant comprises the following substitutions E6Q, G8D, A14P, N15D, E47K, S48E, R51P, A88H, N91H, A130V, E179Q and R189V.

* * * * *

SEQUENCE LISTING

<160> NUMBER OF SEQ ID NOS: 10

<210> SEQ ID NO 1
<211> LENGTH: 194
<212> TYPE: PRT
<213> ORGANISM: Humicola insolens

<400> SEQUENCE: 1

Gln Leu Gly Ala Ile Glu Asn Gly Leu Glu Ser Gly Ser Ala Asn Ala
1               5                   10                  15

Cys Pro Asp Ala Ile Leu Ile Phe Ala Arg Gly Ser Thr Glu Pro Gly
            20                  25                  30

Asn Met Gly Ile Thr Val Gly Pro Ala Leu Ala Asn Gly Leu Glu Ser
        35                  40                  45

His Ile Arg Asn Ile Trp Ile Gln Gly Val Gly Gly Pro Tyr Asp Ala
    50                  55                  60

Ala Leu Ala Thr Asn Phe Leu Pro Arg Gly Thr Ser Gln Ala Asn Ile
65                  70                  75                  80

Asp Glu Gly Lys Arg Leu Phe Ala Leu Ala Asn Gln Lys Cys Pro Asn
                85                  90                  95

Thr Pro Val Val Ala Gly Gly Tyr Ser Gln Gly Ala Ala Leu Ile Ala
            100                 105                 110

Ala Ala Val Ser Glu Leu Ser Gly Ala Val Lys Glu Gln Val Lys Gly
        115                 120                 125

Val Ala Leu Phe Gly Tyr Thr Gln Asn Leu Gln Asn Arg Gly Gly Ile
    130                 135                 140

Pro Asn Tyr Pro Arg Glu Arg Thr Lys Val Phe Cys Asn Val Gly Asp
145                 150                 155                 160

Ala Val Cys Thr Gly Thr Leu Ile Ile Thr Pro Ala His Leu Ser Tyr
            165                 170                 175

Thr Ile Glu Ala Arg Gly Glu Ala Ala Arg Phe Leu Arg Asp Arg Ile
            180                 185                 190

Arg Ala

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Ala Ala Val Asp Ser Asn His Thr Pro Ala Val Pro Glu Leu Val Ala
1               5                   10                  15

Arg

<210> SEQ ID NO 3
<211> LENGTH: 42
<212> TYPE: DNA
<213> ORGANISM: Artificial Sequence
<220> FEATURE:
<223> OTHER INFORMATION: Primer

<400> SEQUENCE: 3
gagtactatc ttgcatttgt actaggagtt tagtgaactt gc                    42

<210> SEQ ID NO 4
<211> LENGTH: 16
<212> TYPE: DNA
<213> ORGANISM: Artificial Sequence
<220> FEATURE:
<223> OTHER INFORMATION: Primer

<400> SEQUENCE: 4
gacgccctgg atccag                                                 16

<210> SEQ ID NO 5
<211> LENGTH: 87
<212> TYPE: DNA
<213> ORGANISM: Artificial Sequence
<220> FEATURE:
<223> OTHER INFORMATION: Primer
<221> NAME/KEY: misc_feature
<222> LOCATION: (43)..(43)
<223> OTHER INFORMATION: n denotes a, g, c or t
<221> NAME/KEY: misc_feature
<222> LOCATION: (46)..(46)
<223> OTHER INFORMATION: n denotes a, g, c or t
<221> NAME/KEY: misc_feature
<222> LOCATION: (49)..(49)
<223> OTHER INFORMATION: n denotes a, g, c or t

<400> SEQUENCE: 5
cggaacatct ggatccaggg cgtcrstggc ccttacrmdd mwncdnygnc dmbdaacdht    60
kyrccgcggg gcacctcgca ggccaac                                        87

<210> SEQ ID NO 6
<211> LENGTH: 41
<212> TYPE: DNA
<213> ORGANISM: Artificial Sequence -continued

```
<220> FEATURE:
<223> OTHER INFORMATION: Primer

<400> SEQUENCE: 6
atggttatgg atttcgggga ttcttcgagc gtcccaaaac c          41

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
gagtactatc ttgcatttgt ac                              22

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
atggttatgg atttcgggga ttc                             23

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
taggagttta gtgaacttgc                                 20

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
ttcgagcgtc ccaaaacc                                   18
```